(12) United States Patent
Cummings

(10) Patent No.: US 8,628,562 B2
(45) Date of Patent: *Jan. 14, 2014

(54) MEDICAL DEVICE DELIVERY SYSTEM

(75) Inventor: Charles Cummings, Reisterstown, MD (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/413,512

(22) Filed: Mar. 6, 2012

(65) Prior Publication Data

US 2012/0172966 A1   Jul. 5, 2012

Related U.S. Application Data

(63) Continuation of application No. 12/140,796, filed on Jun. 17, 2008, now Pat. No. 8,128,676, which is a continuation of application No. 10/842,384, filed on May 10, 2004, now Pat. No. 7,387,640, which is a continuation of application No. 09/681,157, filed on Feb. 1, 2001, now Pat. No. 6,736,839.

(51) Int. Cl.
*A61F 2/06* (2013.01)
*A61F 11/00* (2006.01)

(52) U.S. Cl.
USPC .......................... 623/1.11; 606/108

(58) Field of Classification Search
USPC ................... 623/1.11, 1.23; 606/108
See application file for complete search history.

(56) References Cited

U.S. PATENT DOCUMENTS

| | | | |
|---|---|---|---|
| 4,665,918 A | 5/1987 | Garza et al. |
| 5,163,905 A | 11/1992 | Don Michael |
| 5,443,907 A | 8/1995 | Slaikeu et al. |
| 5,534,007 A | 7/1996 | St. Germain et al. |
| 5,702,364 A | 12/1997 | Euteneuer et al. |
| 5,713,860 A | 2/1998 | Kaplan et al. |
| 5,733,267 A | 3/1998 | Del Toro |
| 5,772,669 A | 6/1998 | Vrba |
| 5,788,707 A | 8/1998 | Del Toro et al. |
| 5,833,706 A | 11/1998 | St. Germain et al. |
| 5,957,930 A | 9/1999 | Vrba |
| 6,017,577 A | 1/2000 | Hostettler et al. |
| 6,176,849 B1 | 1/2001 | Yang et al. |
| 6,221,467 B1 | 4/2001 | Nazarova |
| 6,736,839 B2 | 5/2004 | Cummings |
| 7,387,640 B2 | 6/2008 | Cummings |
| 2001/0034549 A1 | 10/2001 | Bartholf et al. |

*Primary Examiner* — Bruce E Snow
(74) *Attorney, Agent, or Firm* — Seager, Tufte & Wickhem LLC

(57) ABSTRACT

A medical device delivery system comprises an inner tube, a medical device disposed about a portion of the distal region of the inner tube, a medical device sheath disposed about the medical device, a medical device sheath retraction device extending proximally from the medical device sheath and an outer sheath disposed about a portion of the medical device sheath retraction device. The distal end of the outer sheath terminates at least one medical device length proximal of the medical device. The medical device sheath is movable relative to the outer sheath and relative to the inner tube.

18 Claims, 4 Drawing Sheets

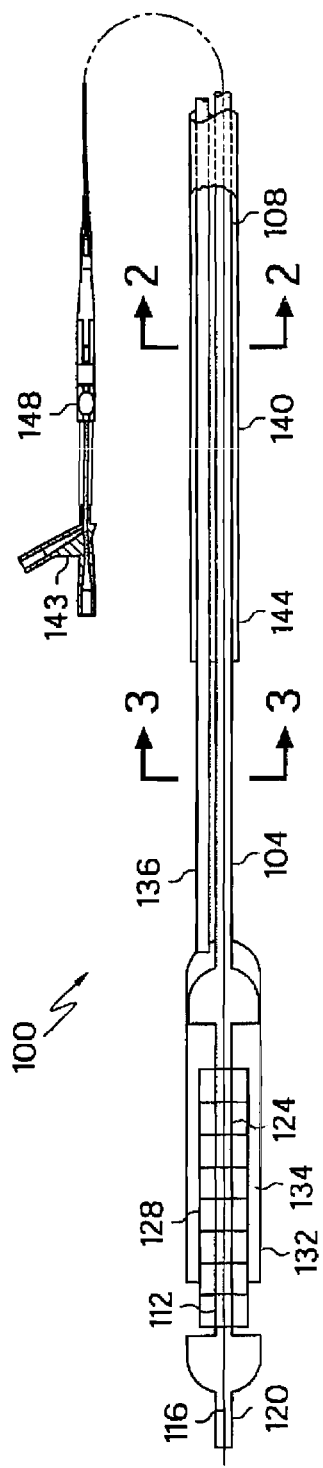
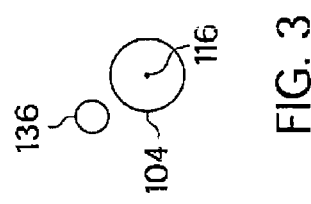
FIG. 1
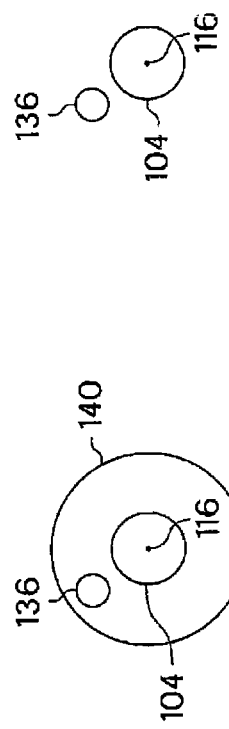
FIG. 2
FIG. 3

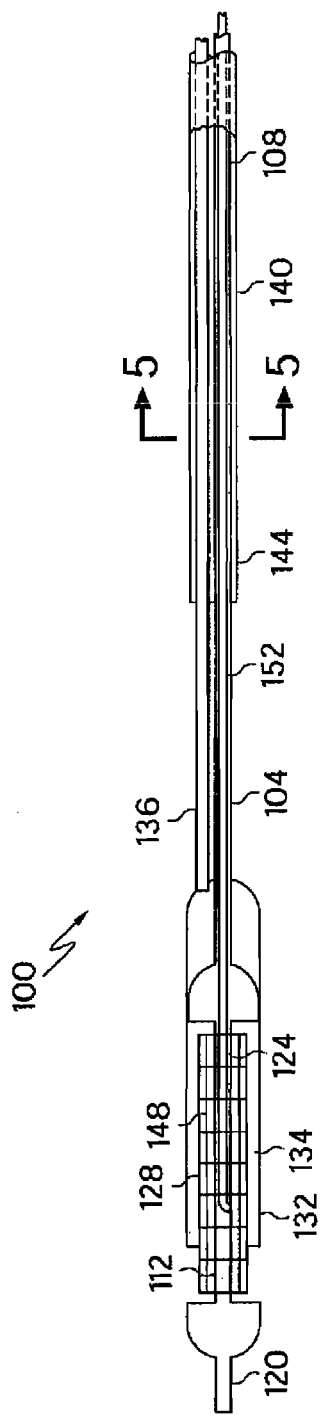
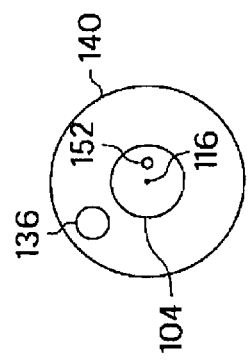
FIG. 4
FIG. 5

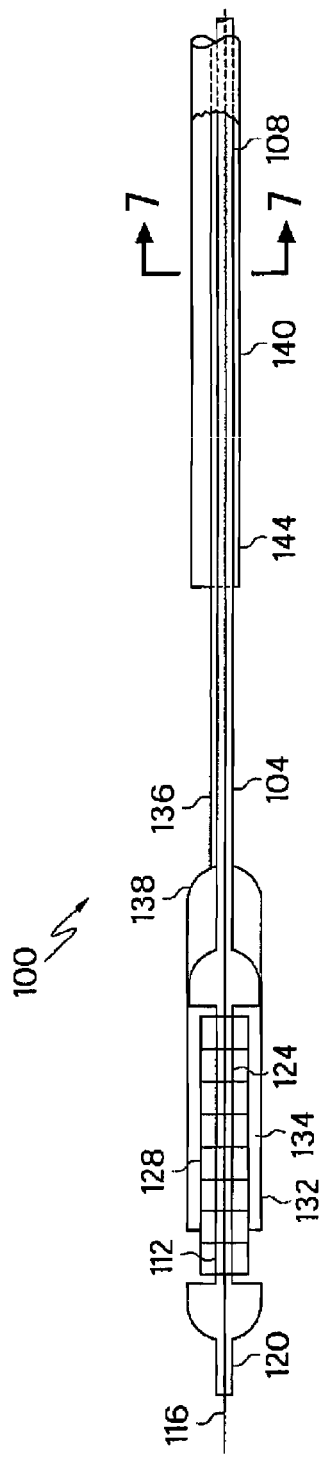
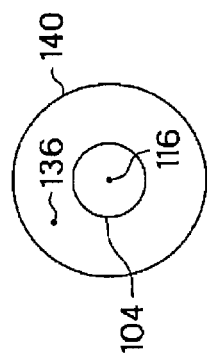
FIG. 6
FIG. 7

MEDICAL DEVICE DELIVERY SYSTEM

CROSS-REFERENCE TO RELATED APPLICATIONS

This application is a continuation of co-pending U.S. application Ser. No. 12/140,796, filed Jun. 17, 2008; which is a continuation of U.S. application Ser. No. 10/842,384, filed May 10, 2004, now U.S. Pat. No. 7,387,640; which is a continuation of U.S. application Ser. No. 09/681,157, filed Feb. 1, 2001, now U.S. Pat. No. 6,736,839, the entire disclosures of which are all incorporated herein by reference.

FIELD OF THE INVENTION

This invention relates to a medical device delivery system. The medical device delivery system has a host of uses including as a stent delivery catheter system, such as the kind used in percutaneous transluminal angioplasty (PTA) or percutaneous transluminal coronary angioplasty (PTCA) procedures. The delivery system employs a retractable sheath which exposes a medical device for deployment.

BACKGROUND OF INVENTION

In typical PTA or PTCA procedures, a guiding catheter is percutaneously introduced into the cardiovascular system of a patient and advanced through the aorta until the distal end is in the desired artery or vessel. Using fluoroscopy, a guide wire is then advanced through the guiding catheter and across the site to be treated in the coronary artery. A balloon catheter is advanced over the guide wire to the treatment site. The balloon is then expanded to reopen the artery. The catheter may have a guide wire lumen which is as long as the catheter (over the wire) or it may be a rapid exchange catheter wherein the guide wire lumen is substantially shorter than the catheter. Alternatively, a fixed wire balloon may be used. This device features a guide wire which is affixed to the catheter and cannot be removed.

To help prevent arterial closure, repair dissection, or prevent restenosis, a physician can implant an intravascular prosthesis, or a stent, for maintaining vascular patency inside an artery or other vessel at the lesion.

Stents are also used for a variety of other purposes including maintaining the patency of any physiological conduit including but not limited to arteries, veins, vessels, the biliary tree, the urinary tract, the alimentary tract, the tracheobronchial tree, the genitourinary system, and the cerebral aqueduct.

For the purposes of this disclosure stents and medical devices may be considered to include any stent, covered stent or prosthesis or any medical device system, grafts or biologic device.

The stent may either be self-expanding or balloon expandable. For the latter type, the stent is often delivered on a balloon and the balloon is used to expand the stent. The self-expanding stents may be made of shape memory materials such as nitinol or constructed of regular metals but of a design which exhibits self-expansion characteristics.

In certain known stent delivery catheters, a stent and an optional balloon are positioned at the distal end of the catheter, around a core lumen. The stent and balloon are held down and covered by a sheath or sleeve. When the distal portion is in its desired location of the targeted vessel the sheath or sleeve is retracted in a proximal direction on the catheter to expose the stent. After the sheath is removed, the stent is free to self-expand or be expanded with a balloon.

In a stent deployment system which utilizes a retractable sheath, retraction of the sheath may result in inaccurate placement of the stent for a variety of reasons including, but not limited to, the interaction of the sheath and guide catheter upon retraction. One way of dealing with this is to make the retractable sheath long enough so that it will be contained in the guide catheter at all times. This increases system profile, reduces flexibility and creates excess friction upon sheath retraction.

Another way of dealing with this issue is described in commonly assigned U.S. Pat. No. 5,772,669. The stent delivery system disclosed therein comprises, in a catheter having a proximal outer shaft, a retractable distal sheath concentrically arranged around a stent receiving portion of the catheter and a pull back means operatively connected to the distal sheath. The catheter is further arranged so that the retractable sheath or a member connected thereto is pulled into the proximal outer shaft of the catheter during refraction of the distal sheath thereby freeing the loaded stent.

All U.S. patents and applications all other published documents mentioned anywhere in this application are incorporated herein by reference in their entirety.

Without limiting the scope of the invention in any way, the invention is briefly summarized in some of its aspects below.

SUMMARY OF INVENTION

In one embodiment, the invention is directed to a medical device or stent delivery system comprising an inner tube having a proximal region and a distal region and a medical device or stent receiving region at the distal end of the inner tube for receiving a medical device or stent thereabout. The system further comprises a medical device or stent sheath disposed about the medical device or stent receiving region. The medical device or stent sheath is movable relative to the inner tube. A medical device or stent sheath retraction device extends proximally from the medical device or stent sheath. An outer sheath is disposed about the inner tube. The outer sheath has a proximal and a distal end, and is disposed about a portion of the medical device or stent sheath retraction device. The distal end of the outer sheath terminates proximal of the medical device or stent receiving region. The medical device or stent sheath is movable relative to the outer sheath.

In another embodiment, the invention provides a stent delivery system which comprises an inner tube with a stent disposed about a portion of the distal region of the inner tube and a stent sheath disposed about the stent. The stent sheath is movable relative to the inner tube. A stent sheath retraction device extends proximally from the stent sheath. An outer sheath is disposed about a portion of the stent sheath retraction device. The outer sheath is characterized by a length which does not exceed the difference in length between the inner tube and twice the length of the stent. The outer sheath is located proximal to the stent sheath. The stent sheath is movable relative to the outer sheath.

In yet another embodiment, the invention provides a stent delivery system which comprises an inner tube with a stent disposed about a portion of the distal region of the inner tube, a stent sheath disposed about the stent, a stent sheath retraction device extending proximally from the stent sheath and an outer sheath disposed about a portion of the stent sheath retraction device. The outer sheath is characterized by a length which does not exceed the difference between the length of the inner tube and the length of the stent. The outer sheath is located proximal to the stent sheath. The stent sheath is movable relative to the outer sheath and to the inner tube.

In yet another embodiment, the invention provides for a stent delivery system which comprises an inner tube with a stent disposed about a portion of the distal region of the inner tube, a stent sheath disposed about the stent, a stent sheath retraction device extending proximally from the stent sheath and an outer sheath disposed about a portion of the stent sheath retraction device. The outer sheath terminates at least one stent length proximal of the stent. The stent sheath is movable relative to the outer sheath and the inner tube.

Additional details and/or embodiments of the invention are discussed below.

BRIEF DESCRIPTION OF DRAWINGS

FIG. 1 shows a schematic side view of an embodiment of a stent delivery system according to the invention having a loaded stent including a cross-sectional view of the distal portion thereof and a side view of the proximal end of a stent delivery system according to the invention showing the manifold portion thereof.

FIG. 2 shows a transverse cross-sectional view of the stent delivery system of FIG. 1 taken along line 2-2.

FIG. 3 shows a transverse cross-sectional view of the stent delivery system of FIG. 1 taken along line 3-3.

FIG. 4 shows a schematic side cross-sectional view of the distal portion of a stent delivery system in accordance with one embodiment of the invention.

FIG. 5 shows a transverse cross-sectional view of the stent delivery system of FIG. 4 taken along line 5-5.

FIG. 6 shows a schematic side cross-sectional view of the distal portion of a stent delivery system in accordance with one embodiment of the invention.

FIG. 7 shows a transverse cross-sectional view of the stent delivery system of FIG. 6 taken along line 7-7.

DETAILED DESCRIPTION

Figure 8:
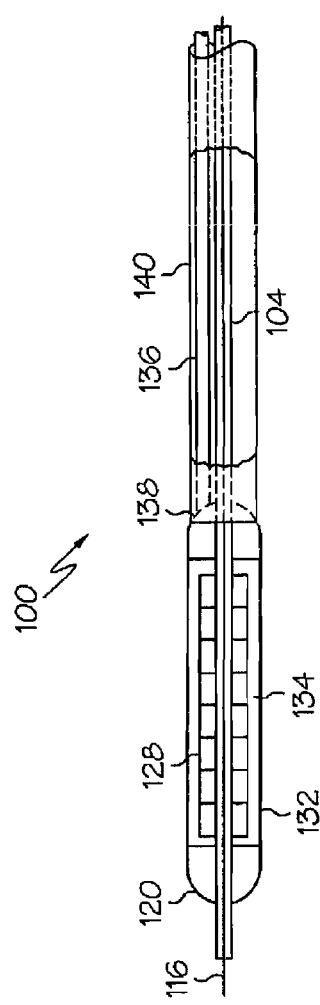
FIG. 8 shows a schematic side cross-sectional view of the distal portion of a stent delivery system in accordance with one embodiment of the invention.

While this invention may be embodied in many different forms, there are shown in the drawings and described in detail herein specific embodiments of the invention. The present disclosure is an exemplification of the principles of the invention and is not intended to limit the invention to the particular embodiments illustrated.

For the purposes of this disclosure, the term stent refers to stents, stent-grafts, grafts and other endoluminal prostheses whether self-expanding, balloon expandable, self-expanding and balloon expandable or otherwise expandable as are known in the art.

In one embodiment, the invention is directed to a stent delivery system, shown generally at 100 in FIG. 1. System 100 includes an inner tube 104 with a proximal end 108 and a distal end 112. Distal end 112 terminates in tip 120 which may be attached thereto or may be a part of the inner tube itself. Inner tube 104 may optionally have a guidewire 116 extending therethrough.

A medical device receiving region 124 is located at distal end 112 of inner tube 104. As shown in FIG. 1, medical device receiving region is a stent receiving region. Stent 128 is shown disposed about stent receiving region 124.

Also disposed about stent receiving region 124 of inner tube 104 is stent sheath 132. Stent sheath 132 provides for a stent chamber 134 in which stent 128 resides. Stent sheath 132 has a hypotube 136 extending proximally therefrom to the proximal end of the stent delivery system. Hypotube 136 serves as a stent sheath retraction device. Hypotube 136 has an opening therein allowing for the delivery of a flush fluid to stent chamber 134. Hypotube 136 and stent sheath 132 may be formed of one piece construction or may be joined together adhesively or otherwise.

Stent delivery system 100 further comprises an outer sheath 140 which extends from the distal end of the stent delivery system. Outer sheath 140 is disposed about a portion of inner tube 104 and a portion of hypotube 136 and terminates proximal to stent sheath 132.

As shown in the embodiment of FIG. 1, distal end 144 of outer sheath 140 is separated from proximal end of stent sheath 132 by at least the length of the stent.

In use, the distal end of stent delivery system 100 is inserted in a bodily vessel. Stent receiving region 124 with stent 128 received thereabout is advanced to a desired region in a vessel. Stent sheath 132 is then retracted in a proximal direction by sliding hypotube 136 proximally using slide 141 in manifold 143 so that the stent sheath no longer covers the stent, thereby allowing for the deployment of the stent. Desirably, stent sheath 132 is refracted until it abuts distal end 144 of outer sheath 140.

For the sake of clarity, FIG. 2 shows the stent delivery system in a transverse cross-section taken through outer sheath 140 along line 2-2 of FIG. 1 and FIG. 3 shows the stent delivery system in a transverse cross-section taken distal to outer sheath 140 along line 3-3 of FIG. 1.

Stent 128 may self-expand upon retraction of the sheath or may be expanded by the inflation of a balloon located underneath the stent (not shown in FIG. 1). Thereafter, the stent delivery system is withdrawn with the stent deployed in the desired location in the bodily vessel.

The embodiment of FIG. 4 is similar to that of FIG. 1 and further comprises a balloon 148 disposed about stent receiving region 124 underneath stent 128. Balloon 148 is supplied with an inflation fluid via inflation lumen 152 extending in inner tube 104. Although not shown in FIG. 2, the stent delivery system may further comprise a guidewire as is shown in FIG. 1. Other configurations of balloons and inflation lumens as are known in the art may also be employed.

For the sake of clarity, FIG. 5 shows the stent delivery system in a transverse cross-section taken through outer sheath 140 along line 5-5 of FIG. 4 Note that in FIG. 5, guidewire 116, not present in FIG. 4, is shown.

In another embodiment of the invention, as shown in FIG. 6, a pull wire 136 extending from stent sheath 132 serves as a retraction device rather than the hypotube shown in FIG. 1. Pull wire 136 is desirably connected to pull collar 138 which, in turn, is connected to stent sheath 132. In all other respects, stent delivery catheter 100 shown in FIG. 6 is identical to that shown in FIG. 1.

FIG. 7 shows a transverse cross-sectional view of the stent delivery system of FIG. 6 taken along line 7-7.

In another embodiment of the invention shown in FIG. 8, stent delivery catheter 100 includes a lengthier outer sheath 140 which extends to stent sheath 132 when stent sheath 132 covers stent 128. Stent sheath 132 is retracted proximally by pulling on pull wire 136 which is attached by pull collar 138 to stent sheath 132.

In addition to the over-the-wire embodiments shown in FIGS. 1-8, the inventive stent delivery system may also be provided in a rapid-exchange configuration. In the embodiment shown at 100 in FIG. 9 guidewire 116 enters inner tube 104 through guidewire port 154 at distal end 144 of outer sheath 140. Inner tube 104 extends from guidewire port 154 to tip 120 of the stent delivery system 100. Guidewire 116 extends through inner tube 104.

Figure 9:
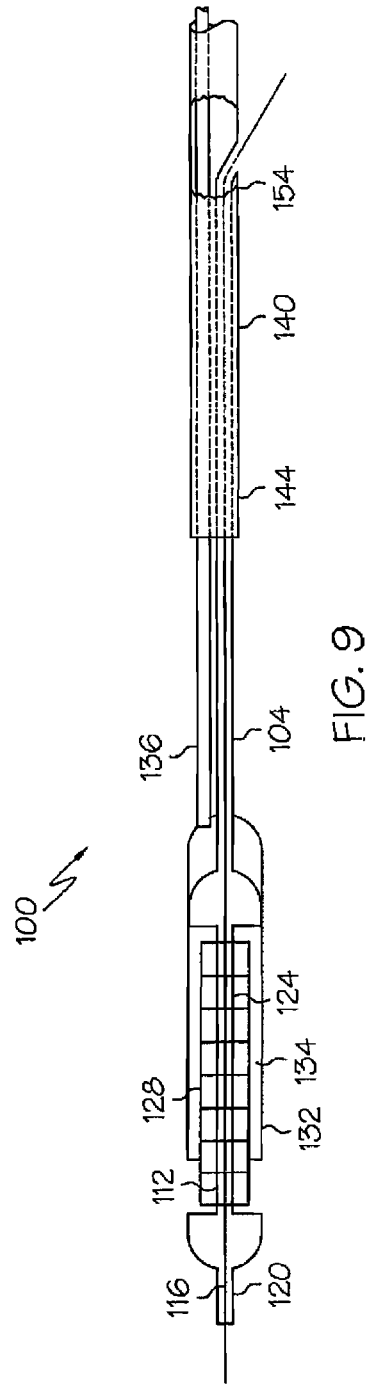
FIG. 9 shows a side cross-sectional view of the distal portion of a stent delivery system.

With the exception that the stent delivery system of FIG. 9 is a rapid-exchange system and the stent delivery system of FIG. 1 is an over-the-wire system, the stent delivery system shown in FIG. 9 is used in a manner identical to that of FIG. 1. Other details of rapid-exchange catheters may be found in U.S. Pat. No. 5,534,007 and U.S. Pat. No. 5,833,706.

The inventive stent delivery systems may also be made in fixed wire form. The stent delivery system of FIG. 1, for example, may have a fixed wire extending from tip 120 rather than a removable guidewire. Additional details of fixed-wire catheters may be found in U.S. Pat. No. 5,702,364.

More generally, the invention is directed to a medical device delivery system which comprises an inner tube having a medical device receiving region at the distal end of the inner tube for receiving a medical device thereabout and a medical device sheath disposed about the medical device receiving region of the inner tube. A medical device sheath retraction device, for example, a pull wire or a hypotube, extends proximally from the medical device sheath. An outer sheath is disposed about a portion of the medical device sheath retraction device. The outer sheath terminates proximal of the medical device receiving region. The medical device sheath is movable relative to the outer sheath and to the inner tube.

The system may be adapted for use with a medical device such as a stent, for example, a self-expanding, balloon expandable or combination self-expanding and balloon expandable stent. The system may also be used for delivery of other medical devices for use in the body as well including, but not limited to, ultrasonic devices, laser devices, vena cava filters, implantable drug delivery devices and the like.

Desirably, the outer sheath terminates at least one medical device length proximal of the medical device however other lengths can be used. In the case of a medical device only a portion of which must be exposed for use in the body, the medical device length is considered to be that portion of the device which must be exposed for use.

The medical device delivery system may be adapted for use in an over-the-wire configuration, in a rapid exchange configuration or fixed wire form.

The outer sheath of the medical device delivery system in general and stent delivery system in particular in its various embodiments may have a roughened surface to anchor the outer sheath in the vessel and to counteract any retraction wire adjustments.

The stent delivery system may also comprise various coatings as are known in the art, including lubricious coatings to facilitate movement of the various parts of the system. More information concerning suitable coatings may be found in U.S. Pat. No. 5,443,907, and U.S. application Ser. Nos. 08/382,478, 09/306,939 and 09/316,502, now U.S. Pat. Nos. 6,017,577, 6,221,467 and 6,176,849, respectively.

An advantage of one embodiment of the medical device delivery system disclosed herein is the reduction in frictional forces on retraction of the medical device sheath. In at least some of the embodiments disclosed herein, the medical device sheath only encounters friction as it slides over the medical device (for example, a stent). As soon as the medical device has been cleared, the frictional forces associated with retraction of the medical device sheath disappear almost entirely as the medical device sheath does not contact the outer sheath. This allows for increased accuracy in deployment of medical devices such as stents as the jumping movement that typically occurs when deploying a stent with a stent delivery system employing a full length sheath is substantially reduced. Other means by which this may reduce jump include but are not limited to reduction of recoil of the catheter and reduction of kinetic energy.

In addition to its medical uses, the instant invention may also prove to be of utility for non-medical uses as well. To that end, the invention is also directed to a device delivery system comprising an inner tube having a proximal region and a distal region and a device receiving region at the distal end of the inner tube for receiving a device thereabout. The system further comprises a device sheath disposed about the device receiving region. The device sheath is movable relative to the inner tube. The system further comprises a device sheath retraction apparatus extending proximally from the device sheath. The outer sheath is disposed about the inner tube and about a portion of the device sheath retraction apparatus. The distal end of the outer sheath terminates proximal of the device receiving region. The device sheath is movable relative to the outer sheath.

It is contemplated that the invention may prove useful where it is desirable to deliver a device to a location within a tube, pipe or conduit while protecting the device during delivery. Possible applications for the system include plumbing and electrical.

In addition to being directed to the specific combinations of features claimed below, the invention is also directed to embodiments having other combinations of the dependent features claimed below and the features described above.

This completes the description of the preferred and alternate embodiments of the invention. Those skilled in the art may recognize other equivalents to the specific embodiment described herein which equivalents are intended to be encompassed by the claims attached hereto.

What is claimed is:

1. A stent delivery system, comprising:
   an inner member having a proximal region, a distal region, and a stent receiving region at a distal end of the inner member for receiving a stent thereabout;
   a stent sheath having a proximal end, the stent sheath being disposed about the stent receiving region, the stent sheath being movable relative to the inner member;
   a stent sheath retraction device extending proximally from the stent sheath to a proximal end of the stent delivery system, wherein the stent sheath retraction device is a hypotube or a pull back wire;
   an outer sheath disposed about the inner member, the outer sheath having a proximal end and a distal end, the distal end of the outer sheath terminating proximal of the stent receiving region, the stent sheath being movable relative to the outer sheath;
   wherein the outer sheath is disposed about a portion of the stent sheath retraction device;
   wherein the distal end of outer sheath is separated from the proximal end of the stent sheath by at least a length of a stent when the stent sheath is in an extended position; and
   wherein the stent sheath retraction device and the inner member are the only structures extending between the proximal end of the stent sheath and the distal end of the outer sheath.

2. The stent delivery system of claim 1, wherein the inner member is an inner tube.

3. The stent delivery system of claim 2, wherein the outer sheath has a length that does not exceed the difference in the length of the inner tube and twice the length of the stent, the distal end of the outer sheath being located proximal to the stent sheath, the stent sheath being movable relative to the outer sheath.

4. The stent delivery system of claim 1, wherein the hypotube is capable of delivering a fluid to the stent.

5. The stent delivery system of claim 1, wherein the stent is self-expanding.

6. The stent delivery system of claim 1, further comprising:
   a balloon disposed about the inner tube and underneath the stent; and
   an inflation lumen in fluid communication with the balloon for supplying an inflation fluid to the balloon, and wherein the stent is balloon expandable.

7. The stent delivery system of claim 1, wherein the stent sheath and hypotube are integrally formed.

8. The stent delivery system of claim 1, wherein the stent delivery system is an over-the-wire system.

9. The stent delivery system of claim 1, wherein the stent delivery system is a rapid-exchange system.

10. The stent delivery system of claim 1, wherein the proximal end of the stent sheath abuts the distal end of the outer sheath when in a retracted position.

11. The stent delivery system of claim 1, the outer sheath having a length of at least half the length of the hypotube.

12. The stent delivery system of claim 1, wherein a length of the inner member remains exposed to a body lumen between the distal end of the outer sheath and the proximal end of the stent sheath when the stent sheath is extended, and the stent delivery system is inserted into the body lumen.

13. A stent delivery system, comprising:
   an inner member having a stent receiving region;
   a stent disposed on the stent receiving region, the stent having a length;
   a stent sheath having a proximal end, the stent sheath being disposed about the stent receiving region;
   wherein the stent sheath is movable relative to the inner member;
   a stent sheath retraction device extending proximally from the stent sheath;
   an outer sheath disposed about the inner member, the outer sheath having a proximal end and a distal end;
   wherein the distal end of the outer sheath extends to a position that is proximal of the stent receiving region;
   wherein the stent sheath is movable relative to the outer sheath;
   wherein the outer sheath is disposed about a portion of the stent sheath retraction device;
   wherein a region of the inner member and a region of the stent sheath retraction device, between the distal end of the outer sheath and the proximal end of the stent sheath, are uncovered by any other structure of the stent delivery system; and
   wherein the distal end of outer sheath is separated from the proximal end of the stent sheath by at least the length of the stent.

14. The stent delivery system of claim 13, wherein the stent is a self-expanding stent.

15. The stent delivery system of claim 13, wherein the stent sheath retraction device includes a tubular member.

16. The stent delivery system of claim 13, wherein the stent sheath retraction device includes a pull wire.

17. The stent delivery system of claim 13, wherein the outer sheath has a length that is smaller than the length of the inner member.

18. A stent delivery system, comprising:
   an inner member having a stent receiving region;
   a deployment sheath having a proximal end, the deployment sheath being configured to shift between an extended position where the deployment sheath is disposed about the stent receiving region and a retracted position;
   a deployment sheath retraction device extending proximally from the deployment sheath;
   an outer sheath disposed about the inner member, the outer sheath having a distal end;
   wherein the distal end of the outer sheath extends to a position that is proximal of the stent receiving region;
   wherein the outer sheath is disposed about a portion of the deployment sheath retraction device; and
   wherein the distal end of outer sheath is separated from the proximal end of the deployment sheath, wherein a length of the inner member remains exposed to a body lumen between the distal end of the outer sheath and the proximal end of the deployment sheath when the deployment sheath is extended, and the stent delivery system is inserted into the body lumen.

* * * * *